United States Patent [19]

Kadlec et al.

[11] 4,371,456

[45] Feb. 1, 1983

[54] CATALYST FOR DIRECT HYDRATION OF ETHYLENE TO ETHYL ALCOHOL AND PROCESS FOR PREPARATION THEREOF

[75] Inventors: Vlastimil Kadlec, Litvinov; Vojtěch Grosser, Rudolice; Jakub Rosenthal, Mezibori u Litvinova, all of Czechoslovakia

[73] Assignee: Chemopetrol, koncernovy podnik, Chemicke zavody ceskoslovenskosovetskeho pratelstvi, Litvinov, Czechoslovakia

[21] Appl. No.: 255,221

[22] Filed: Apr. 17, 1981

[30] Foreign Application Priority Data

Apr. 18, 1980 [CS] Czechoslovakia .................. 2734-80

[51] Int. Cl.$^3$ .......................... B01J 21/08; B01J 27/16
[52] U.S. Cl. ..................................... 252/435; 568/896
[58] Field of Search ..................... 252/435; 568/896

[56] References Cited

U.S. PATENT DOCUMENTS

| | | | |
|---|---|---|---|
| 3,311,568 | 3/1967 | Kumenko | 252/435 |
| 3,459,678 | 8/1969 | Hagemeyer et al. | 568/896 |
| 4,038,211 | 7/1977 | Frampton | 252/435 |
| 4,297,241 | 10/1981 | Kavasmaneck et al. | 252/435 |

*Primary Examiner*—W. J. Shine

[57] ABSTRACT

A novel catalyst for hydration of ethylene to ethyl alcohol comprises active synthetic silicon dioxide as a base having deposited thereon natural kieselguhr and phosphoric acid. The catalyst is prepared by precipitative silicon dioxide from sodium silicate with hydrochloric acid, filtering the precipitate, admixing it with natural kieselguhr and phosphoric acid and annealing the resultant composition.

6 Claims, No Drawings

CATALYST FOR DIRECT HYDRATION OF ETHYLENE TO ETHYL ALCOHOL AND PROCESS FOR PREPARATION THEREOF

This invention relates to a novel catalyst for the direct hydration of ethylene to ethyl alcohol and to a method for the preparation thereof. More particularly, the present invention relates to a catalyst for the direct hydration of ethylene to ethyl alcohol which evidences enhanced mechanical strength, stability and resistance to deactivation in the hydration process.

It has been recognized by those skilled in the art that catalysts capable of effecting the direct hydration of ethylene to ethyl alcohol must evidence the prerequisites of high efficiency, good mechanical properties and the ability, under standard conditions, to produce an alcohol-aqueous condensate having a high concentration of ethyl alcohol over a long time period.

Studies have revealed that catalysts meeting these prerequisites include carriers comprising natural kieselguhr from various European and overseas sources. Unfortunately, such kieselguhrs typically contain varying amounts of foreign matter, namely, metal oxides, and it has been customary to remove the oxides or substantially reduce the content thereof in accordance with standard procedures. Typically, this end is attained by acid refining the kieselguhr at elevated temperatures and either atmospheric or elevated pressure in the presence of inorganic acies. Following, the kieselguhr is filtered, washed, dried, formed, thermally treated, saturated with phosphoric acid and re-dried. Although hydration catalysts so prepared are capable of yielding ethyl alcohol of high standards, the procedures employed suffer from certain technical and economic limitations. Thus, from a technical standpoint, the production process is intricate and requires inconvenient equipment specially prepared for the acid refining process and the filtration step. Furthermore, the process is not economical due to the demand for chemicals used in the refining process and due to the inherent loss of the most valuable fine kieselguhr particles during filtration. Accordingly, these prior art catalysts do not meet present demands.

A second category of catalysts for effecting hydration of ethylene to ethyl alcohol is also known. This catalyst comprises as its active substance phosphoric acid deposited upon a silica gel carrier. Under moderate conditions over short time cycles the phosphoric acid catalyst is presently used with some degree of success, the mechanical strength and resistance to deactivation being of lesser importance. However, this catalyst has a limited life cycle.

In the present industrial environment, the producer of ethyl alcohol utilizing the direct hydration of ethylene process seeks to operate the production unit at a temperature less than 300° C. with a yield in excess of 180 grams of ethyl alcohol in 1 liter of alcohol-aqueous condensate. It is also considered advantageous to attain high mechanical strength and resistance to deactivation to the extent that the catalyst is capable of being used for several cycles including regeneration for a time period of at least 10,000 hours.

In accordance with the present invention, these ends are effectively attained and the prior art limitations obviated by means of a novel combined catalyst evidencing enhanced mechanical strength, stability and resistance to deactivation which comprises a silicon dioxide base having deposited thereon active phosphoric acid containing active synthetic silicon dioxide, natural kieselguhr and phosphoric acid. The described catalyst contains active synthetic silicon and natural kieselguhr in a weight ratio ranging from 1:0.2 to 1:4 with a general preference for a range of from 1:0.5 to 1:1, and from 20–50 weight percent phosphoric acid a general preference being for a phosphoric acid weight percentage of 30–40%.

The described catalyst may conveniently be prepared by reacting a sodium silicate solution with hydrochloric acid in the presence of an electrolyte, thereby resulting in the precipitation of a material which is filtered and washed and either directly thereafter or following during drying is admixed with natural kieselguhr, water and a bonding agent. The resultant mixture now in a plastic condition is then extruded to shape and either dried or directly pressed, annealed at a temperature in excess of 800° C., preferably 1000° to 1300° C., and then saturated with phosphoric acid and dried.

The resultant activated and stabilized catalyst is then suited for the direct hydration of ethylene to ethyl alcohol in a continuous reactor at a temperature less than 300° C. and a pressure of 7 to 8 MPa, the molecular ratio of water to ethylene being 0.5 to 0.7. The described catalyst has been found to be particularly effective at temperatures no higher than 280° C. with a molecular ratio of water to ethylene less than 0.6.

An example of the application of the novel catalyst described herein is set forth below. It will be understood by those skilled in the art that the described embodiment is solely for purposes of exposition and it is not be construed as limiting.

EXAMPLE

Three types of catalysts were prepared for use in synthesizing ethyl alcohol by the direct hydration of ethylene, two of such catalysts being prepared in accordance with the preparative technique of the invention and the third in accordance with conventional prior art techniques. The characteristics of these catalysts are set forth in the table which follows. Hydration of ethylene to ethyl alcohol using these catalysts was effected under severe conditions in order to accentuate the differences in their function.

TABLE

| Catalyst No. | 1 | 2 | 3 |
|---|---|---|---|
| Type | Conventional Comprising natural Kieselguhr | Invention Comprising synthetic $SiO_2$ and natural Kieselguhr in ratio of 1:1 | Invention Comprising synthetic $SiO_2$ and natural Kieselguhr in ratio of 1:4 |
| Mode of Preparation | By extruding, annealing at 1150° C. | By extruding, annealing at 1050° C. | By extruding, annealing at 1200° C. |
| Characteristics: | | | |
| $H_3PO_4$ weight % | 38.5 | 35.2* | 37.2* |

TABLE-continued

| Catalyst No. | 1 | 2 | 3 |
|---|---|---|---|
| crushing strength N | 26.4 | 68.5 | 64.5 |
| bulk density g/l | 840 | 730 | 752 |
| Direct Hydration of Ethylene: | | | |
| pressure MPa | 8.0 | 7.5 | 7.4 |
| temperature °C. | 290 | 280 | 280 |
| ratio $H_2O:C_2H_4$ | 0.6 | 0.58 | 0.59 |
| test time hours | 300 | 300 | 300 |
| initial productivity g/l | 214 | 210 | 210 |
| final productivity g/l | 165 | 211 | 205 |
| final carbon content weight % | 0.6 | 0.3 | 0.4 |

Remark:
*At the end of the test the content of phosphoric acid was 21%.

Analysis of the data set forth in the Table reveals that catalysts prepared in accordance with the invention evidenced a significantly higher mechanical strength and greater stability than the prior art catalyst, the latter being evident from the difference in ethyl alcohol productivity at the start and end of the testing. Additionally, the final carbon content at the end of testing is indicative of higher resistance to deactivation than that of the prior art catalyst.

What is claimed is:

1. Catalyst for direct hydration of ethylene to ethyl alcohol consisting of phosphoric acid on a silicon dioxide base characterized in that said catalyst consists of active synthetic silicon dioxide and natural kieselguhr in a weight ratio ranging from 1:0.2 to 1:4, and phosphoric acid in an amount ranging from 20–50 weight percent based on the weight of the catalyst.

2. Catalyst in accordance with claim 1, wherein the weight ratio of silicon dioxide to kieselguhr ranges from 1:0.5 to 1:1.

3. Catalyst in accordance with claim 1, wherein the weight percent of phosphoric acid ranges from 30–40 weight percent based on the weight of the final composition.

4. Process for the preparation of a catalyst in accordance with claim 1 which comprises the steps of (a) reacting a solution of sodium silicate with hydrochloric acid in the presence of an electrolyte, so resulting in the formation of a precipitate, (b) filtering and washing said precipitate, (c) mixing said precipitate with natural kieselguhr, water and a bonding agent, (d) extruding the resultant plastic composition and pressing, (e) annealing said composition at a temperature in excess of 800° C., and (f) saturating said annealed composition with phosphoric acid and drying.

5. Process in accordance with claim 4, wherein the annealing temperature ranges from 1000° to 1300° C.

6. Process in accordance with claim 4, wherein said precipitate is dried prior to being mixed with natural kieselguhr, water and a bonding agent.

* * * * *